(12) United States Patent
Hakalehto

(10) Patent No.: US 7,517,665 B1
(45) Date of Patent: Apr. 14, 2009

(54) METHOD AND APPARATUS FOR CONCENTRATING AND SEARCHING OF MICROBIOLOGICAL SPECIMENS

(75) Inventor: Elias Hakalehto, Kasarmikatu 12 C 1, FIN-70110 Kuopio (FI)

(73) Assignee: Elias Hakalehto, Kuopio (FI)

( * ) Notice: Subject to any disclaimer, the term of this patent is extended or adjusted under 35 U.S.C. 154(b) by 0 days.

(21) Appl. No.: 09/564,644

(22) Filed: May 3, 2000

(51) Int. Cl.
  *C12M 1/02* (2006.01)
  *C12M 1/36* (2006.01)
  *C12M 1/00* (2006.01)

(52) U.S. Cl. .................. 435/29; 435/818; 435/286.6; 435/4

(58) Field of Classification Search ............ 435/293.1, 435/299.2, 304.1, 309.1, 818, 286.6, 29
See application file for complete search history.

(56) References Cited

U.S. PATENT DOCUMENTS 4,009,078 A * 2/1977 Wilkins et al. ............ 205/778
4,054,491 A * 10/1977 Lindgren ................... 435/34
4,673,396 A * 6/1987 Urbaniak ................... 604/211

FOREIGN PATENT DOCUMENTS

EP 0964913 B1 * 10/2001
WO WO95/02049 * 1/1995

* cited by examiner

*Primary Examiner*—Walter D Griffin
*Assistant Examiner*—Lydia Edwards
(74) *Attorney, Agent, or Firm*—Pillsbury Winthrop Shaw Pittman LLP

(57) ABSTRACT

The invention relates to a method for enriching and examining microbiological samples. In which method microbes are brought into a syringe or equivalent. In a method according to the invention the enrichment culture of microbes is accomplished inside a syringe or equivalent. An apparatus according to the invention comprises a syringe or equivalent and into the syringe or the plunger (3) of the syringe a lead-through is manufactured in order to conduct gas or gas mixture to or from the syringe.

12 Claims, 1 Drawing Sheet

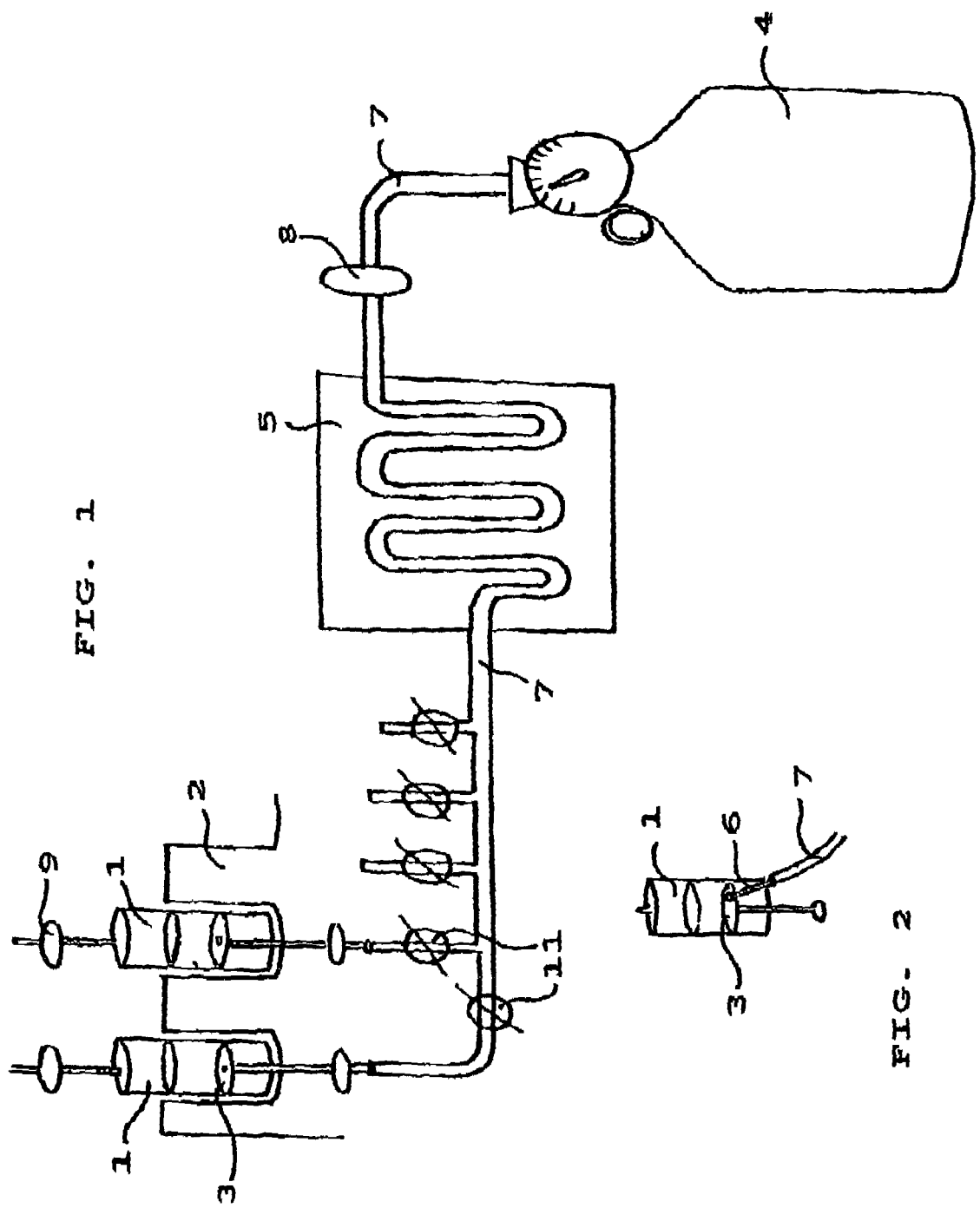

METHOD AND APPARATUS FOR CONCENTRATING AND SEARCHING OF MICROBIOLOGICAL SPECIMENS

The invention relates to a method for enriching and examining microbiological samples, in which method microbes are brought into a syringe or equivalent. The invention also relates to an apparatus for applying the method, the apparatus consisting of a syringe or equivalent.

Collecting microbiological sweep samples is an important part of hygiene control in industrial establishments, hospitals, laboratories and other places where the hygiene of the establishment, apparatuses and equipment is an absolute operational prerequisite. Sweep samples may also be collected from e.g. human skin or mucous membrane for clinical diagnostics.

Usually a microbiological sweep sample or a picked sample is suspended from sampling means into a buffer solution or any other appropriate solution, where it may be further examined and handled. In this case a usual method for acquiring additional information on possible microbes adhered to the sampling means is so-called subculture. This is usually accomplished by transferring the microbial suspension to be examined to a liquid culture substrate or to a solid culture substrate (e.g. a Petri dish). Thereafter the microbes in the culture substrate are incubated for at least some hours, but usually for one or more days, even weeks. During this incubation phase, the microbe to be examined is enriched to such a content that it is possible to indicate it by the indication method in use. A limiting factor for the growth of aerobic organisms during incubation may be for example oxygen. On the other hand, appropriate gases can be used in the incubation of aerobic microbes to achieve and maintain an adequately anaerobic environment. The so-called microaerophilic bacteria (e.g. *Compylobacter* sp.) need small oxygen contents. Also changing contents of gases may, if necessary, be conveyed to the enrichment space.

In some situations rapid completion of a microbiological analysis is crucially important e.g. for the success of a patient's treatment, in choosing cleansing measures in hygiene control, in industrial quality control etc. Many factors have further increased the threat caused by microbes (hospital infections, new human and animal pathogenes, previously unknown industrial microbe contaminants, environmental microbiological pollution etc.). In order to be able to respond to these challenges adequately effectively, so-called rapid diagnostic methods are needed for indicating and identifying microbes.

The method according to international patent application PCT/FI95/00398 is aiming to collect microbiological sweep samples for further examination as easily as possible and in the case of handling pathogenic microbes as safely as possible. The above is achieved with the syringe of the invention (volume e.g. 10-50 ml) which is characterized in that the surface facing away from the plunger rod comprises an adhering substrate for microbes. The adhering substrate on the surface of the plunger may be e.g. cotton, velvet or a similar porous corresponding material that has been sterilized together with the syringe or separately (e.g. an autoclave or by radiating). Biomolecules (e.g. antibodies) that improve the adhesion of certain microbes may also, if necessary, be aseptically immobilized to the adhering substrate surface. By using the syringe and its plunger with adhering substrate surface, one avoids extra handling of microbe-containing liquids by use of a pipette, which increases safety when working with infectious microbes. The sample is transferred from the syringe onto a separate culture substrate where it is grown in a usual way. The sample may also be collected into the syringe in a usual way by sucking liquid into the syringe. In this way for example a blood sample is usually accomplished. A liquid sample may naturally be collected directly into the syringe without an injection needle or by use of a specially manufactured longer tip or a tube or similar.

The object of the present invention is to provide a method and an apparatus with which the work of further analysing microbiological samples is speeded up, which leads to fast and reliable indication, identification, enrichment etc.

The objects of the invention are achieved by the method and apparatus, which are characterized by what is presented in the patent claim.

The method of the invention is characterized in that the enrichment or other growth of microbes is performed inside the syringe or equivalent. This enrichment takes place in adjusted conditions and the conditions may easily be changed during the enrichment. This makes possible e.g. a safe further inoculation in a desired growth phase, because the growth in the syringe is easy to follow for example visually or using a colour indicator. The use of the syringe and its measure scale make it possible to accomplish microbiological dilution series conveniently. For example a so-called −1 dilution is accomplished by taking a ninefold volume of the dilution solution into the syringe per one sample volume. The syringe is then shaken and 9 volumes, which can be used as a sample in further analysis, are removed, and another 9 volumes of dilution solution are added, which gives a so-called −2 dilution and so on.

It is possible to change the existing conditions in the syringe for example by temperature, pH and gases conducted to the substrate. It is advantageous to use a bubbly gasflow to the substrate, in which flow the composition of the gases may be adjusted, and which also may be used to adjust the temperature and the pH. At the same time the culture is mixed, which improves the even spreading of nutrients into the substrate. It is also easy to add into the syringe, if necessary, more substrate, nutrients, selective factors and other substances in liquid form.

During incubation of aerobic microbes, the diffusion of oxygen is increased by the gas-flow conducted to the syringe, which is important in order to achieve the best possible growth speed as the availability of oxygen is usually the so-called restricting factor in aerobic microbe incubation. Apart for oxygen, also gases like nitrogen and carbon dioxide may be conducted to the substrate. With the help of these, e.g. anaerobic or microaerophilic conditions can be achieved in accordance with the type of microbes needing incubation and enrichment. The partial pressure of differant gases can be used as selective factors. Gases led to the substrate may also be used as carrier gases, which make it possible to transfer to the substrate as aerosols, in a vaporous form or by corresponding means substances that control the culture conditions or the actual cultivation or even inoculate the medium or the culture. To accomplish this, before being transferred to the syringe, the gas may be led through a liquid or a suspension containing the component that is to be added.

From a rapid microbial detection point of view it is crucial that an adequate microbial concentration needed for reliable detection is achieved as quickly as possible. It is possible to achieve this object by using the method according to the invention e.g. for the purpose of carrying out immunological detections. Possible microbial detections, in which the method according to the invention may be used are e.g. hygiene control of interior surfaces, tools and any other surfaces, mould determination from any surfaces, hygiene control of carcases (e.g. *Salmonella* detection) and many other microbiological sweep sample and liquid sample detections that are required in industrial establishments, health care and environmental analytics.

When exploiting the method according to the invention in using the syringe used as sampling means for microbe enrichment, in an economical application, an appropriate selective nutrient medium to enrich the microbe may be used as growth medium immediately after sampling. Thus the enrichment may begin safely immediately after the sampling without delays caused by inoculation or transfer of the sample. This is a benefit as microbes with cells in resting state have a lag-phase before bacterial growth. E.g. the lag-phase for *Staphylococcus aureus* bacteria lasts for approximately 1,5 hours.

In hospitals and other equivalent establishments the occurrance of antibiotic resistant microbial strains may be determined from interior surfaces and apparatuses, and from human skin and mucous membranes. Blood samples and any other liquid samples may be examined in a similar way. These may be patient samples or other liquid samples used in hospitals that require microbiological quality examination. During the enrichment, required antibiotics may be added to the medium. Advantages of the method are in this and many other cases besides the simple and straightforward procedure and material savings also security as the transfer of hazardous microbes in laboratories is minimized.

In an economical application of the invention, the temperature, pH and/or other conditions of the culture substrate are adjusted by gas or gas mixture that is conducted to the substrate within the syringe. The gas is conducted into the syringe in a commonly known way. As the temperature during the culture may be adjusted by the gas flow, incubation chambers or equivalent apparatuses are not necessarily needed during the culture. To heat or cool the syringe specific heating or cooling blocks e.g. Peltier elements may be used.

If necessary, exhaust gases may be conducted from the enrichment space of the syringe by a tube via sterilization (e.g. a filter).

In one application of the invention the syringe is placed in a holder tip upwards during enrichment. Alternatively the syringe may be placed in a holder also tip downwards if gas is led to the enrichment space through the tip.

In an economical application of the invention, the growth solution and sample are transferred for further examination with the same syringe where the culture is done. Samples may be transferred in the syringe if necessary, and for this purpose the tip may be manufactured to be closed with a lid, a valve or with any other closing device. Since in enrichment or in other further treatments of samples complicated apparatuses and work phases are not needed, it may be accomplished e.g. in industrial establishments beside the production line under control. Results are gained faster as there is no need for transferring or storing the sample. Also safety risks in regard to transfer and storage are decreased.

The apparatus in accordance with the invention is characterized in, that there is a lead-through or a conduit into the syringe or into the syringe plunger for conducting gas or gas mixture into the syringe. If the rod of the plunger of the syringe is manufactured with a conduit or several conduits in the rod for conducting gas, the culture substrate may be aerated or required gases may be conducted to it in order to enhance during incubation the enrichment of aerobic microbes on one hand and anaerobic on the other hand. This gas may originate from a compressed gas bottle.

Gas may be conducted into the syringe also directly through the plunger e.g. by piercing it with an injection needle to which the gas bottle is connected by a tube or a conduit. An alternative is to conduct the gas into the syringe through a lead-through or a conduit elsewhere in the syringe. The composition of the gas may be altered during the culture e.g. in accordance with the growth phase of the microbe that is being enriched. The gas may be conducted into the syringe through a sterile filter to ensure aseptic conditions. Correspondingly exhaust gas through the tip may be filtered by use of a sterile filter. The tip of the syringe may also be closed for transportation or any other reason with a cap, a lid or a valve.

Alternatively gas may be conducted into the syringe through the tip, in which case another route must be used for exhaust gas, e.g. using a lead-through with a valve or equivalent or through the plunger or the air holes in it with the help of excess pressure. The lead-through may in this case be done using an injection needle through the plunger or the wall of the syringe.

The apparatus according to the invention comprises of a syringe with an economically transparent wall or window frame. Thus it is possible to accomplish microbial growth determination optically or visually e.g. through the wall of the syringe. Thus it is naturally possible to add e.g. indicator colour solution to the growth medium e.g. to indicate the change of pH, which indicates the change of microbial metabolism in the growth medium.

In the following the invention will be described in detail with reference to the accompanying drawings, in which FIG. 1 shows a side view of an application of the apparatus to apply the method characterized in the invention, and FIG. 2 shows a side view of another way for conducting gas into the syringe via a lead-through.

The apparatus shown in FIG. 1 comprises of one or more syringes 1, containing microbiological culture media, which are placed in a holder 2, tip upwards, one or more compressed bottles 4, for storing gases or mixtures of gases, a heating/cooling jacket 5, for incoming gases, wherein the temperature of the gas is adjusted by known means. There is a lead-through in the plunger 3, of the syringe, and to it is connected a conduit 7, through which gas or gas mixture is conducted from a compressed bottle into the syringe. The conduit 7, comprises one or more control valves 11, to adjust incoming gas. Additionally the apparatus comprises of a sterile filter 8, which is placed in the incoming conduit in order to sterilize incoming gas. Exhaust gas is sterilized using another sterile filter 9, which is connected to the tip of the syringe.

In an application as shown in FIG. 2, gas is conducted through the plunger 3, using a separate injection needle 6, or an equivalent. The injection needle comprises a conduit, such as a tube or 7, or a pipe, that is connected to a compressed bottle as described above.

In the following, the method will be described by working phases while collecting samples:

Microbes are adhered to the adhering substrate, which is either moistened (water, buffer solution) or dry and attached to the surface of the plunger 3, by sweeping the examined surface to and fro with this plunger surface. Thereafter the plunger 3, is placed in an empty syringe 1, receiver and air is pushed out through an opening in the tip of the receiver. Alternatively a sample may be collected into a syringe by sucking liquid into the syringe by normal means. The sampling should be carried out in a way that is well represents the studied object and that the sampled area is large enough.

Thereafter the receiver is filled by suction with a required volume of liquid (e.g. buffer solution, water or culture solution) and thereafter with some air in order to help with the mixing procedure. The apparatus is thereafter swung and shaken as a test tube to ensure microbial detachment into the liquid solution.

In the case that culture solution is used as a solution, the syringe may be left upside down and placed in a holder 2, in a growth temperature that is appropriate for the enrichment of the microbe intended to be indicated. In the case that gas is conducted by alternative means through the tip of the syringe, the syringe is naturally not left upside down for enrichment. The culture solution may also be added into the syringe after the microbe has first been suspended into another solution. The adjustment of temperature (or pH or any equivalent parameter) may be done by means of gas conducted through a lead-through in the plunger of the syringe. Buffered salt solution, extract solution (e.g. diluted acid or base solution), detergent solution or any equivalent solution may be used for suspending.

Suspension may be used for inoculation or it may be transferred either directly or after cultivation to the culture medium or to any other further examinations. In this case e.g. microbe identification may be done using ordinary biochemical, immunological or genetic methods. In enriching the microbe to be detected and its antigen, it is possible to exploit e.g. a method characterized in Finnish Patent 93742.

Although the invention is described herein with reference to applications it will be appreciated that the invention may be realized in a variety of ways within the scope of the inventive idea and the appended claims.

The invention claimed is:

1. A method for enriching and examining microbiological samples, comprising the following steps:

(a) drawing microbes into a syringe in the form of a liquid substrate, (b) enriching the microbes inside the syringe of step (a), and (c) conducting a gas or gas mixture as a bubbly gas flow into the liquid substrate of step (b).

2. A method according to claim 1, further comprising using a gas flow for mixing a culture of microbes or for aeration or for achieving anaerobic or microaerophilic conditions or for controlling the temperature of the substrate.

3. A method according to claim 1, further comprising using a culture substrate inside a syringe or equivalent so that it is selective to required microbes.

4. A method according to claims 1, 2 or 3, wherein a sample containing microbes is collected into the syringe prior to the addition of growth medium.

5. A method according to claims 1, 2 or 3, wherein a syringe is placed tip upwards in a holder for the enrichment period.

6. A method according to claims 1, 2 or 3, wherein a syringe is placed tip downwards in a holder for the enrichment period and in that gas is conducted into the syringe through the tip.

7. A method according to claims 1, 2 or 3, wherein a substrate solution where the microbe growth has taken place in the syringe or equivalent is transferred for further examination using the same syringe where the culture was accomplished.

8. A method according to claims 1, 2 or 3, wherein dilutions of the culture is the liquid substrate according to microbiological dilution series may be accomplished in the syringe.

9. An apparatus for applying a method for enriching and examining microbiological samples, comprising one or more syringes, each of which comprises a plunger, wherein a lead-through or conduit is manufactured in each syringe or the plunger of the syringe in order to conduct gas or gas mixture into the liquid substrate inside the syringe, or to conduct gas or gas mixture out of the syringe;

one or more compressed bottles which are connected via one or more connecting tubes or pipes to said syringe for conducting gas or gas mixture from the bottle(s) into the syringe; and, a heating/cooling jacket in contact with said connecting tubes or pipes, in which the temperature of gas in said connecting tubes or pipes is adjusted as required prior to conducting it into the syringe.

10. An apparatus for applying a method for enriching and examining microbiological samples, comprising one or more syringes, each of which comprises a plunger, wherein a lead-through or conduit is manufactured in each syringe or the plunger of the syringe in order to conduct gas or gas mixture into the liquid substrate inside the syringe, or to conduct gas or gas mixture out of the syringe; and, one or more compressed bottles which are connected via one or more connecting tubes or pipes to said syringe for conducting gas or gas mixture from the bottle(s) into the syringe, wherein the plunger comprises plunger rod that comprises one or more conduits that conduct gas in or out of the syringe.

11. An apparatus for applying a method for enriching and examining microbiological samples, comprising one or more syringes, each of which comprises a plunger, wherein a lead-through or conduit is manufactured in each syringe or the plunger of the syringe in order to conduct gas or gas mixture into the liquid substrate inside the syringe, or to conduct gas or gas mixture out of the syringe;

one or more compressed bottles which are connected via one or more connecting tubes or pipes to said syringe for conducting gas or gas mixture from the bottle(s) into the syringe; and, a lid, cap or valve to close the tip of the syringe.

12. An apparatus for applying a method for enriching and examining microbiological samples, comprising one or more syringes, each of which comprises a plunger, wherein a lead-through or conduit is manufactured in each syringe or the plunger of the syringe in order to conduct gas or gas mixture into the liquid substrate inside the syringe, or to conduct gas or gas mixture out of the syringe;

one or more compressed bottles which are connected via one or more connecting tubes or pipes to said syringe for conducting gas or gas mixture from the bottle(s) into the syringe; and, one or more sterile filters in order to conduct incoming and/or exhaust gas or gas mixture through a sterile filter.

* * * * *